(12) United States Patent
Fukuzawa et al.

(10) Patent No.: US 9,775,552 B2
(45) Date of Patent: Oct. 3, 2017

(54) LANCING DEVICE

(71) Applicant: ARKRAY, INC., Kyoto (JP)

(72) Inventors: Masahiro Fukuzawa, Kyoto (JP); Shinsui Murakami, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 252 days.

(21) Appl. No.: 14/496,946

(22) Filed: Sep. 25, 2014

(65) Prior Publication Data
US 2015/0094750 A1 Apr. 2, 2015

(30) Foreign Application Priority Data

Sep. 27, 2013 (JP) .................................. 2013-201511

(51) Int. Cl.
*A61B 5/151* (2006.01)
*A61B 5/15* (2006.01)
(52) U.S. Cl.
CPC ........ *A61B 5/15117* (2013.01); *A61B 5/1513* (2013.01); *A61B 5/1519* (2013.01); *A61B 5/150022* (2013.01); *A61B 5/150106* (2013.01); *A61B 5/15113* (2013.01); *A61B 5/150152* (2013.01); *A61B 5/15194* (2013.01); *A61B 5/150412* (2013.01); *A61B 5/150503* (2013.01)
(58) Field of Classification Search
CPC ........ A61B 5/150022; A61B 5/150106; A61B 5/150412; A61B 5/15113; A61B 5/15117; A61B 5/1519
See application file for complete search history.

(56) References Cited

U.S. PATENT DOCUMENTS

2008/0262388 A1 10/2008 List et al.
2011/0196261 A1* 8/2011 Robbins ............. A61B 5/15186
600/583

FOREIGN PATENT DOCUMENTS

| DE | 102011017275 A1 | 10/2012 |
|---|---|---|
| EP | 0898936 A2 | 3/1999 |
| EP | 1797822 A1 | 6/2007 |
| EP | 1992285 A1 | 11/2008 |
| JP | 2013-517056 A | 5/2013 |
| WO | 2006/029320 A1 | 3/2006 |

OTHER PUBLICATIONS

The extended European search report issued by the European Patent Office dated Jan. 28, 2015, which corresponds to European Patent Application No. 14186619.4-1506 and is related to U.S. Appl. No. 14/496,946.

* cited by examiner

*Primary Examiner* — Julie A Szpira
(74) *Attorney, Agent, or Firm* — Studebaker & Brackett PC

(57) ABSTRACT

A lancing device includes a housing, a lancing unit capable of reciprocating relative to the housing, an elastic member for causing the lancing unit to reciprocate, and a resistance generator for applying resistance to the lancing unit in motion. The reciprocating motion of the lancing unit includes a puncture section or interval and a retreat section following the puncture section. The puncture section includes a puncture point at which a lancing element of the lancing unit can prick the skin of a human subject, for example. The resistance generator is configured to apply a greater resistance to the lancing unit in the retreat section than in the puncture section.

12 Claims, 16 Drawing Sheets

LANCING DEVICE

BACKGROUND OF THE INVENTION

1. Field of the Invention

The present invention relates to a lancing device provided with an lancing element capable of reciprocating for pricking the skin of a human subject, for example.

2. Description of the Related Art

To conduct medical testing such as measurement of the glucose level, it is necessary to obtain a sample of blood from the human subject. Conventionally, to obtain a blood sample, use is made of a lancing device provided with a lancing element (such as a needle) to prick the skin (see JP-A-2013-517056, for example).

FIG. 22 depicts a known lancing device. The illustrated lancing device X includes a housing 91 in which a lancet holder 92 and a spring 93 are accommodated. The housing 91 may be made of a resin and have a generally cylindrical shape. The lancet holder 92 has the same central axis as the housing 1, and includes a tubular member for holding a lancet (not shown) provided with a needle extending in the x1 direction. The spring 93 is provided for causing the lancet holder 92 to advance in the x1 direction. For causing the lancet holder 92 to retreat in the x2 direction, the lancing device X may preferably include another spring. In use, a lancet is fixed into the lancet holder 92, and then the compressed spring 93 is released to propel the lancet holder 92 forward in the x1 direction. Hence, the needle of the lancet will prick the skin of the subject, and thereafter the lancet holder 92 is caused to retreat in the x2 direction by the additional spring.

In the lancing device X, a projection 92a is formed on the lancet holder 92, and a guide slit 91a is formed on the housing 91. The projection 92a extends to the outside of the housing 91 through the slit 91a. Since the projection 92a is guided along the guide slit 91a, the lancet holder 92 can be properly moved in the advancing direction x1 and the retreating direction x2 without causing positional deviation. The housing 91 includes a cantilevered stopper 91b having a fixed end (x2-side end) and a free end (x2-side end). As seen from the figure, the x1-side end of the guide slit 91a is defined by the stopper 91b. In use, the lancet holder 92 is caused to advance in the x1 direction, and the projection 92a will collide with the stopper 91b, thereby checking the stroke of the lancet holder 92. Since the stopper 91b is cantilevered, the impact of the collision is alleviated. In this manner, it is possible to prevent the lancing element of the lancet (which is held by the lancet holder 92) from pricking the skin with excessive momentum, which contributes to the alleviation of pain the user of the lancing device may feel.

With the known lancing device, however, the lancing holder 92 tends to keep quivering (due to the spring 93 and the additional spring) within the housing after the skin is pricked. Such quivering can make the user uncomfortable with the use of the lancing device.

SUMMARY OF THE INVENTION

The present invention has been proposed under the circumstances described above. It is therefore an object of an embodiment of the present invention to provide a lancing device which the user can use without feeling uncomfortable.

According to an embodiment, there is provided a lancing device provided with: a housing; a lancing unit capable of reciprocating relative to the housing, the reciprocating including an advancing motion and a retreating motion, the lancing unit being provided with a lancing element to prick skin of a subject; an elastic member for causing the lancing unit to reciprocate; and a resistance generator for applying resistance to the lancing unit. A reciprocating motion of the lancing unit includes a puncture section and a retreat section following the puncture section, and the puncture section includes a puncture point at which the lancing element pricks the skin. The resistance generator is configured to apply a greater resistance in the retreat section than in the puncture section.

Preferably, the reciprocating motion of the lancing unit includes an advance section followed by the puncture section, and the resistance generator is configured to apply a greater resistance in the advance section than in the puncture section.

Preferably, the resistance generator is configured to apply a greater resistance in the retreat section than in the advance section when a positional relation between the lacing unit and the housing is same for the retreat section and the advance section.

Preferably, the resistance generator is configured to apply zero resistance in the puncture section.

Preferably, the resistance generator includes a protrusion and a sliding member held in sliding contact with the protrusion in the retreat section, and wherein one of the protrusion and the sliding member is provided on the housing, and the other of the protrusion and the sliding member is provided on the lancing unit.

Preferably, the sliding member is more elastically deformable in a direction in which the sliding member faces the protrusion than is the protrusion.

Preferably, the sliding member includes a fixed end and a free end spaced apart from each other in a reciprocating direction of the lancing unit, the fixed end being adjacent to the protrusion when the lancing unit is at the puncture point, the free end being adjacent to the protrusion when the lancing unit is at an end point of the retreat section. The sliding member is provided with an inclined surface arranged between the fixed end and the free end and coming into sliding contact with the protrusion, the inclined surface being inclined so as to be closer to the protrusion in a direction perpendicular to the reciprocating direction as proceeding from the fixed end toward the free end.

Preferably, the sliding member is configured as an engaging element for engaging the housing and the lancing unit with each other so that the lancing unit is held at the end point of the retreat section.

Preferably, the protrusion is provided on the housing, and the sliding member is provided on the lancing unit.

Preferably, the housing includes an outer frame and an inner frame disposed in the outer frame, and the protrusion is provided on the inner frame.

In another embodiment, the inner frame of the housing has an inner wall surface, and a rib (or a projection on the housing) is formed to extend inwardly from the inner wall surface. On the other hand, the lancing unit is formed with a flange (or a projection on the lancing unit) that is capable of coming into contact with the rib of the inner frame, thereby checking the stroke of the lancing unit relative to the housing.

In another embodiment, the lancing device further includes a setting member provided for setting the lancing unit to a standby state in which the lancing unit is ready to advance for the pricking. In addition, the inner frame of the housing is formed with a slit or a groove elongated along the central axis of the housing (or the lancing device), while the setting member (or an additional intervening member configured to attach the setting member to the inner frame) is formed with a projection capable of coming into engagement with the slit or groove formed in the inner frame. With such arrangements, the stroke of the setting member relative to the housing can be properly defined.

In another embodiment, the inner frame of the housing is made up of two cooperating parts: a lower part (first part) and an upper part (second part) that can be separated from each other in a direction perpendicular to the axis of the housing. In this instance, the above-mentioned slit or groove of the inner frame may be provided by combining two elongated recesses formed in these two parts, respectively.

Other features and advantages of the embodiments will become more apparent from the detailed description given below with reference to the accompanying drawings.

DETAILED DESCRIPTION OF THE PREFERRED EMBODIMENTS

Figure 1:
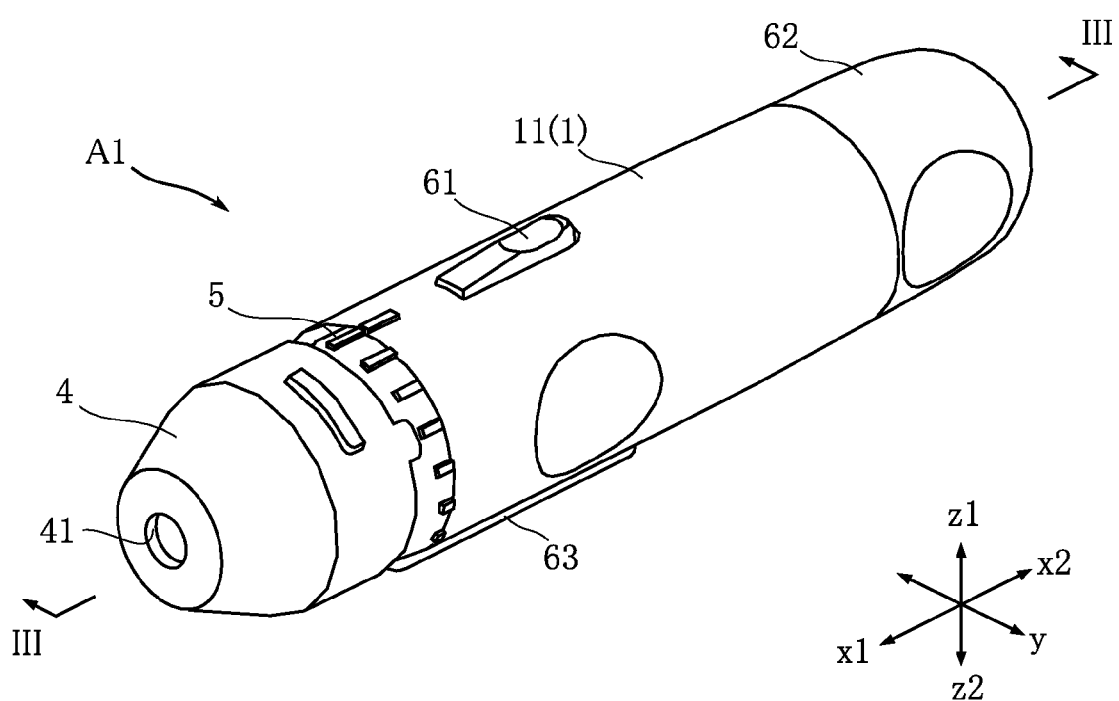
FIG. 1 is a perspective view depicting a lancing device according to an embodiment of the present invention.

Preferred embodiments will be described below with reference to the accompanying drawings.

FIGS. 1-5 show a lancing device A1 according to an embodiment. The lancing device A1 includes a housing 1, a lancing unit 2, a progress spring 31, a retreat spring 32, a cover 4, a spacer 5, a puncture button 61, a setting member 62, a release lever 63 and a slide member 64.

Figure 2:
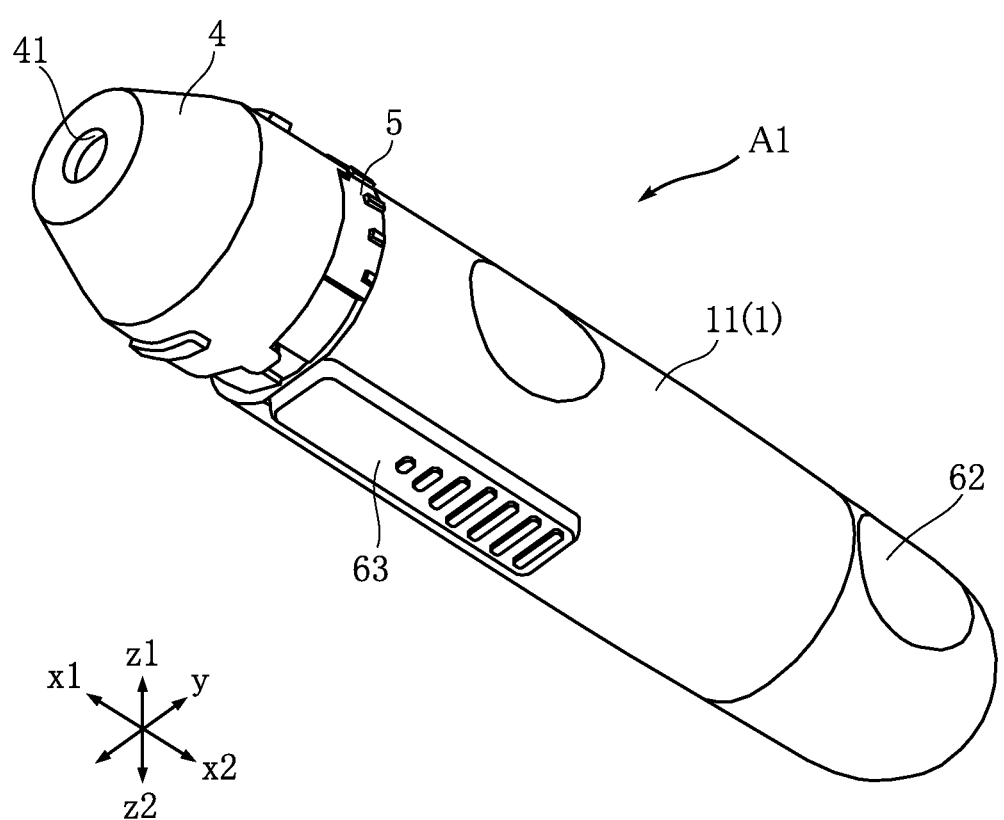
FIG. 2 is another perspective view depicting the lancing device of FIG. 1.
Figure 3:
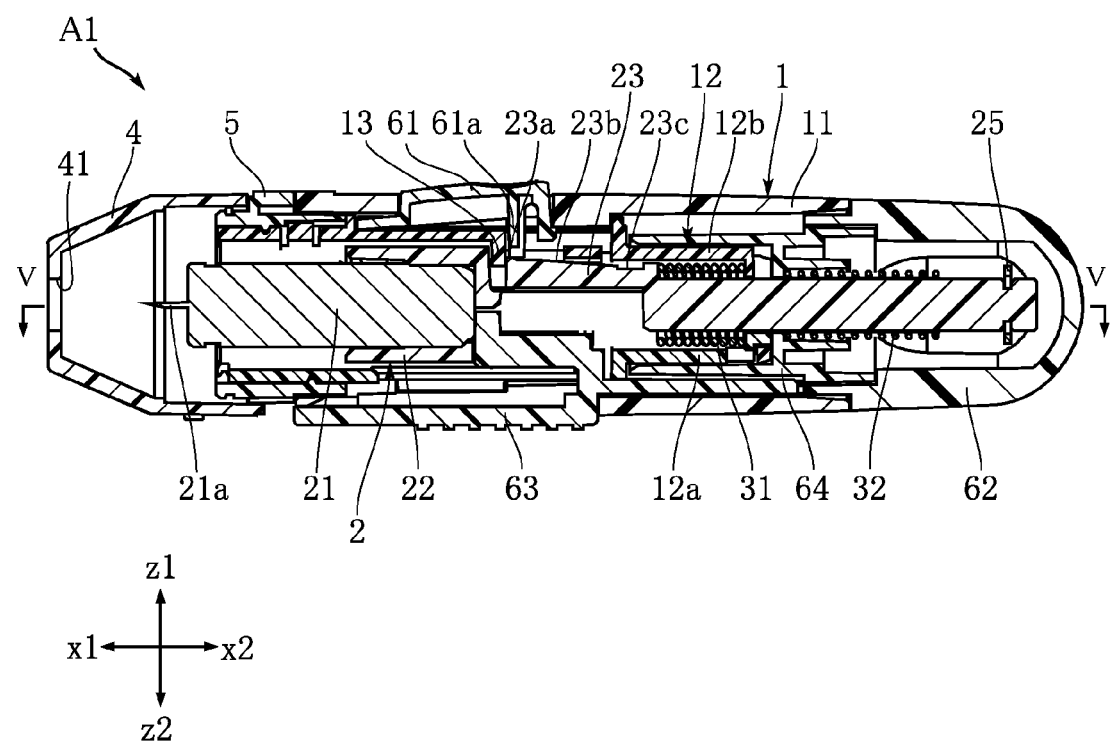
FIG. 3 is a sectional view taken along line III-III in FIG. 1.
Figure 4:
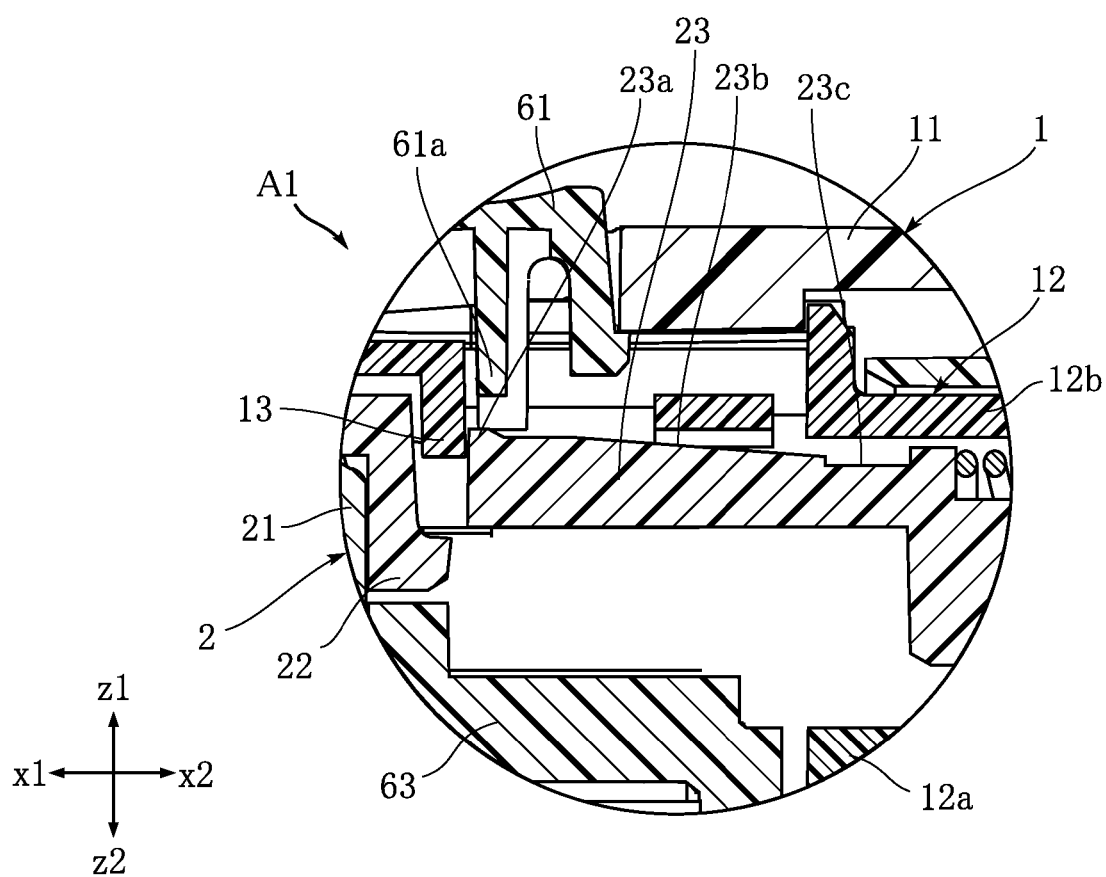
FIG. 4 is an enlarged view depicting some features shown in FIG. 3.
Figure 5:
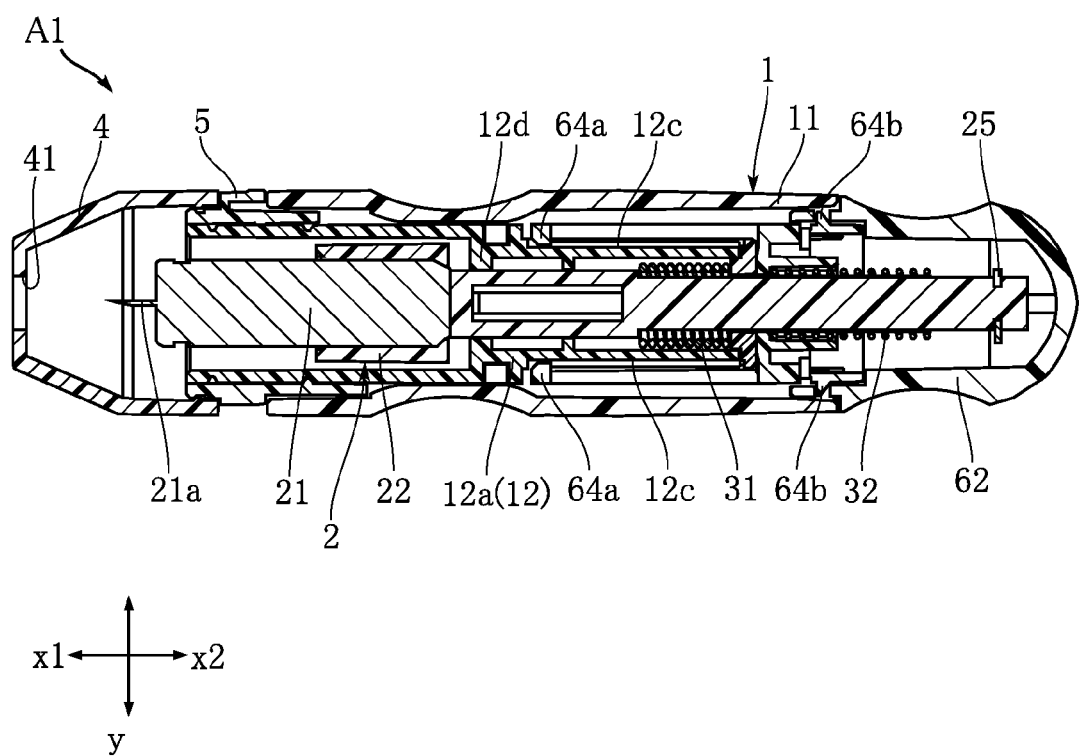
FIG. 5 is a sectional view taken along line V-V in FIG. 3.

FIG. 1 is a perspective view showing the lancing device A1 as viewed from above, and FIG. 2 is a perspective view showing the same lancing device A1 as viewed from below. FIG. 3 is a sectional view taken along the III-III line of FIG. 1, and FIG. 4 is an enlarged sectional view of the lancing device A1. FIG. 5 is a sectional view taken along the V-V line of FIG. 3. In these figures, the advance direction (lancing direction) of the lancing unit 2 corresponds to the x1 direction, and the retreat direction of the lancing unit 2 corresponds to the x2 direction. The z1-z2 direction is perpendicular to the x1-x2 direction, and the z1 direction corresponds to the vertically upward direction, while the z2 direction corresponds to the vertically downward direction. The y direction is perpendicular to both the x1-x2 direction and the z1-z2 direction. FIG. 3-FIG. 5 show a standby state in which the lancing unit 2 is ready to advance for pricking the skin of e.g., a human subject. As explained below, the lancing unit 2 is configured to be movable with respect to the housing 1 within a predetermined range extending in the x1-x2 direction. The lancing unit 2 in the standby state is located at one of the two mutually spaced limit positions of the above-noted range.

The housing 1 provides most of the external form of the lancing device A1. The housing 1 is in a generally cylindrical form having an axis extending in the x1-x2 direction. In the illustrated embodiment, the housing 1 is made up of an outer frame 11 and an inner frame 12. The outer frame 11 is a generally cylindrical member formed as a single unit integrally made of a resin material, for example. The inner frame 12 is a generally cylindrical member disposed in the outer frame 11. The outer frame 11 and the inner frame 12 have a common central axis. The inner frame 12 may be made up of two individual parts that can be engaged with each other. In the illustrated embodiment, the inner frame 12 is constructed by a first part 12a and a second part 12b. The first part 12a provides a generally half portion (lower portion) of the inner frame 12, while the second part 12b provides a generally half portion (upper portion) of the inner frame 12. The first part 12a and the second part 12b are made of a resin material, for example.

It should be noted that the above configuration is only an example for the housing 1. Alternatively, the housing 1 may be formed as a single cylindrical unit, not made up of two (or more) individual parts such as the outer frame 11 and the inner frame 12. Likewise, the inner frame 12 may be formed as a single unit, not made up of two (or more) individual parts such as the first part 12a and the second part 12b.

Figure 7:
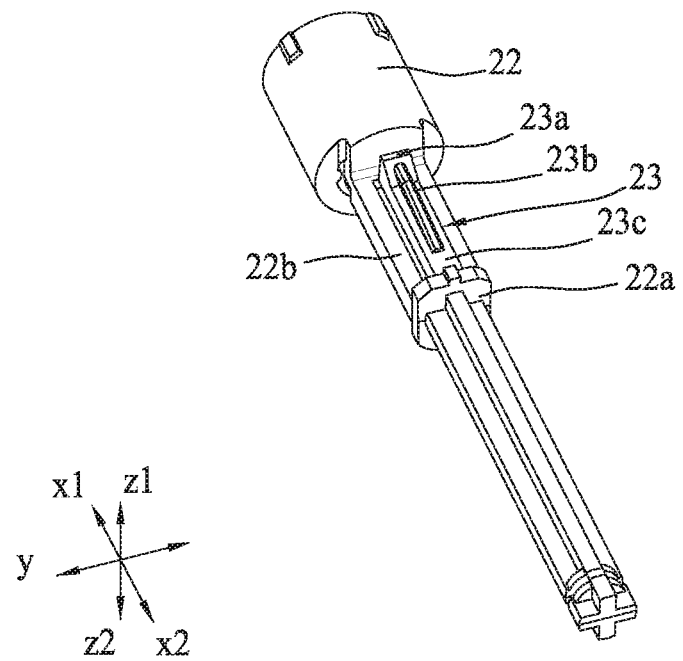
FIG. 7 is a perspective view depicting the lancet holder of the lancing device.

The lancing unit 2 is configured to reciprocate within the housing 1. Specifically, the lancing unit 2 can advance or move forward in the x1 direction, and can also retreat or move backward in the x2 direction. In the illustrated embodiment, the lancing unit 2 includes a lancet 21 and a lancet holder 22. The lancet 21 is provided with a lancing element (a needle 21a in the illustrated embodiment), and can be removably attached to the lancet holder 22. In the illustrated embodiment, the lancet 21 is of a disposable type, which is to be discarded once used. The lancet holder 22 is configured to hold the lancet 21. As shown in FIG. 7, the lancet holder 22 includes a tubular portion which the lancet 21 is fixed into, and an elongated extension extending from the bottom of the tubular portion in the x2 direction. The lancet holder 22 (i.e., the tubular portion and the extension) is formed as a single unit integrally made of a resin material.

The progress spring 31 and the retreat spring 32 are an example of elastic elements. A part of the lancet holder 22 is passed through the progress spring 31 and the retreat spring 32. The progress spring 31 exhibits elasticity to advance the lancing unit 2 in the x1 direction, and the retreat spring 32 exhibits elasticity to retreat the lancing unit 2 in the x2 direction. It should be noted that, for providing the required elasticity, use may be made of any element that can cause the lancing unit 2 to reciprocate in the desired manner. In the illustrated embodiment, two springs are used for moving the lancet body 2 forward and backward. Alternatively, more than two springs or only a single spring may be used. Also, any type of element made of any suitable elastic material may be used instead of the illustrated helical springs as long as the substitute exhibits the desired elasticity.

The cover 4 is located on the x1 side of the housing 1 for closing the open end (that is open in the x1 direction) of the housing 1. A through-hole 41 is formed in the cover 4, so that the needle 21a of the lancing unit 2 can project to the outside through the through-hole 41. When the lancing device A1 is used, the distal end of the cover 4 is brought into contact with the skin of the subject. The cover 4 is formed, for example, of a resin material which may be transparent or non-transparent.

The spacer 5 is disposed between the housing 1 and the cover 4 and is an annular member made of a resin material. The cover 4 is attached to the housing 1 via the spacer 5. The projecting amount of the cover 4 in the x1 direction with respect to the housing 1 is adjustable by changing the circumferential position of the spacer 5 relative to the housing 1. In a different embodiment, the lancing device may not be provided with the cover 4 nor the spacer 5.

The puncture button 61 is operated by the user to advance the lancing unit 2, thereby causing the needle 21a to prick the skin. A portion of the puncture button 61 is exposed to the outside from the outer frame 11 of the housing 1. In the illustrated embodiment, the exposed portion of the puncture button 61 is arranged offset slightly forward (i.e., in the x1 direction) from the longitudinal center of the outer frame 11 of the housing 1. Preferably, the color of the puncture button 61 may be different from the color of the housing 1 for facilitating the use of the lancing device A1.

The setting member 62 is provided for setting the lancing unit 2 in the standby state. In the illustrated embodiment, the setting member 62 is disposed at the rear end of the housing 1 (an end opposite to the cover 4). The user of the lancing device A1 may accidentally push the puncture button 61 when the cover 4 is not in contact with the skin. In such a case, the setting member 62 is used to pull back the lancing unit 2 into the standby state.

The slide member 64 is provided for slidably attaching the setting member 62 to the housing 1.

After the pricking of the skin is performed, the release lever 63 is operated to remove the lancet 21 from the lancet holder 22. The release lever 63 may be made of a resin material, and a portion of the release lever 63 is exposed to the outside from the outer frame 11 of the housing 1. In the illustrated embodiment, the release lever 63 is slidably attached to the housing 1. With the cover 4 removed, the release lever 63 is slid in the x1 direction, thereby detaching the lancet 21 from the lancet holder 22.

Figure 9:
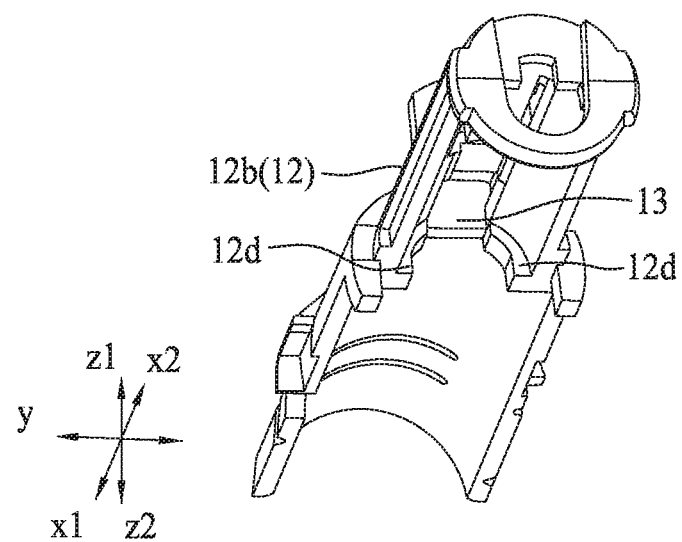
FIG. 9 is a perspective view depicting the upper part of the inner frame of the lancing device.

As shown in FIGS. 3, 4 and 9, a ridge or protrusion 13 is formed on the second part 12b of the inner frame 12. The protrusion 13 is configured to jut out inwardly from the sidewall of the second part 12b. A sliding arm 23 is formed on the lancet holder 22 (see FIGS. 6 and 7). In accordance with the illustrated embodiment, the sliding arm 23 is disposed at the extension of the lancet holder 22. The sliding arm 23 has a free end adjacent to the tubular portion of the lancet holder 22 and a fixed end opposite to the free end. Thus, the sliding arm 23 is configured as a cantilever. In the illustrated embodiment, a combination of the protrusion 13 and the sliding arm 23 provides a "resistance generator" or damper. The resistance generator gives resistance against the reciprocating motion of the lancing unit 2. In the illustrated embodiment, only the frictional force occurring between the protrusion 13 and the sliding arm 23 substantially contributes as resistance acting against the reciprocation of the lancing unit 2. Since the sliding arm 23 is cantilevered, the sliding arm 23 elastically deforms more easily than the protrusion 13 in a direction (z1-z2 direction) in which the protrusion 13 faces the sliding arm 23. Unlike the illustrated embodiment, a portion corresponding to the protrusion 13 may be provided on the lancing unit 2, while a portion corresponding to the sliding arm 23 may be provided on the housing 1. That is, resistance to the reciprocating motion of the lancing unit 2 may be given directly to the lancing unit 2 in itself.

As shown in FIG. 4, the sliding arm 23 is provided with a latch projection 23a, an inclined surface 23b and a recess 23c. The latch projection 23a is disposed at the free end of the sliding arm 23. The latch projection 23a projects in a lateral direction perpendicular to the central axis of the housing 1 (or perpendicular to the lancing direction) and extends away from the central axis (or extends in the z1 direction in FIG. 4). In the z1-z2 direction, the tip (in FIG. 4, the upper end) of the latch projection 23a is located outward of the tip (in FIG. 4, the lower end) of the protrusion 13. In other words, the tip of the latch projection 23a is located farther from the axis of the housing 1 than is the tip of the projection 13. With these arrangements, the latch projection 23a can be in engagement with the protrusion 13 (i.e., a part of the housing 1) when the lancing unit 2 is in the standby state (or when the progress spring 31 is compressed for pricking the skin). As seen from this, the sliding arm 23 also functions as an engaging element to be engaged with the protrusion 13. Unlike the illustrated resistance generator, the lancing unit 2 may be provided with an engaging element to be engaged with the housing 1.

The inclined surface 23b, offset from the latch projection 23a in the x2 direction, is inclined with respect to the z1 direction. More specifically, the inclined surface 23b is inclined so as to go outward (in FIG. 4, in the z1 direction) with increasing distance from the recess 23c in the x1 direction. In the standby state (see FIGS. 3 and 4), the entirety or part of the inclined surface 23b is located outward of the tip (in FIG. 4, the lower end) of the protrusion 13. In the illustrated embodiment, the inclined surface 23b is a single flat plane. Alternatively, the inclined surface 23b may be configured as a curved surface or a combination of non-parallel planes.

The recess 23c is offset from the inclined surface 23b in the x2 direction. That is, the recess 23c is located opposite to the latch projection 23a with respect to the inclined surface 23b. The recess 23c is dented inward, i.e., in a direction approaching the central axis of the housing 1 (in FIG. 4, in the z2 direction). The bottom surface of the recess 23c is located inward than the tip (in FIG. 4, the lower end) of the protrusion 13.

In the illustrated embodiment, the progress spring 31 is disposed between a rear end of the inner frame 12 and a flange portion (adjacent to the fixed end of the sliding arm 23) provided on the extension of the lancet holder 22. When the lancing unit 2 is moved in the retreat direction (x2 direction) relative to the housing 1 (the inner frame 12), the progress spring 31 is compressed. This compression causes the progress spring 31 to save an elastic force for advancing the lancing unit 2 in the lancing direction (x1 direction).

In the illustrated embodiment, a washer 25 is provided on the extension of the lancet holder 22 and near the rear end of the extension. The retreat spring 32 is disposed between the slide member 64 and the washer 25. When the lancing unit 2 moves in the lancing direction relative to the housing 1 (the inner frame 12), the retreat spring 32 is compressed. This compression causes the retreat spring 32 to save an elastic force for moving the lancing unit 2 in the retreating direction (x2 direction) opposite to the lancing direction.

Figure 6:
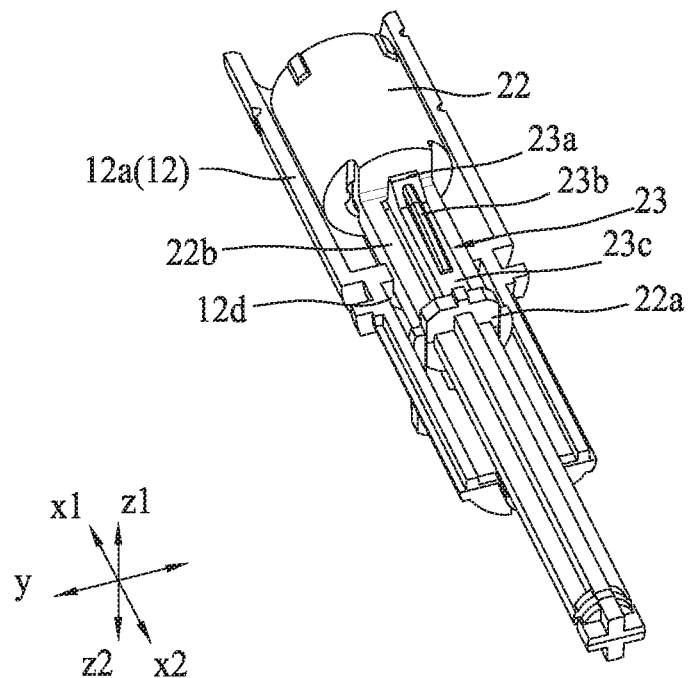
FIG. 6 is a perspective view depicting a lower part of the inner frame and a lancet holder of the lancing device.

Next, arrangements for defining the reciprocating motion of the lancing unit 2 to the housing 1 will be described. FIG. 6 is a perspective view depicting the first part 12a and the lancet holder 22. As shown in the figure, the first part 12a is formed with a rib 12d, and the lancet holder 22 is formed with a flange 22a. FIG. 7 is a perspective view depicting the lancet holder 22. The flange 22a is located at a middle position in the longitudinal direction (x1-x2 direction) of the lancet holder 22, and is in the form of a plate perpendicular to the longitudinal direction (i.e., the normal direction of the plate is parallel to the longitudinal direction).

Figure 8:
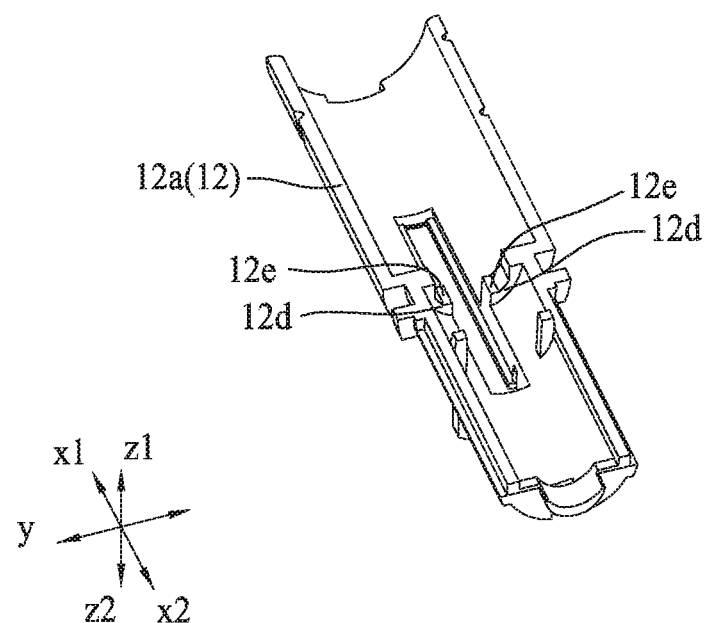
FIG. 8 is a perspective view depicting the lower part of the inner frame of the lancing device.

FIG. 8 is a perspective view depicting the first part 12a. The rib 12d is located at a middle position in the longitudinal direction of the first part 12a, and projects inward. As shown in FIG. 6, the rib 12d is offset from the flange 22a in the lancing direction (x1 direction). The rib 12d and the flange 22a are arranged to overlap each other as viewed in the lancing direction. The motion of the lancing unit 2 relative to the housing 1 in the lancing direction is checked by the flange 22a coming into contact with the rib 12d.

FIG. 9 is a perspective view depicting the second part 12b. As shown in the figure, the second part 12b is also formed with a rib 12d. The rib 12d of the second part 12b and the rib 12d of the first part 12a are located at the same position along the lancing direction. Thus, with the inner frame 12 properly assembled (i.e., with the first part 12a and the second part 12b properly coupled), the rib 12d of the inner frame 12 allows a relatively thin part (the part between the tubular portion and the flange 22a) of the lancet holder 22 to pass through, while preventing the passage of the flange 22a.

The rib 12d of the first part 12a (see FIG. 8) is located immediately under the protrusion 13 (see FIG. 9), i.e., spaced apart from the protrusion 13 in the z2 direction. As shown in FIG. 8, the rib 12d of the first part 12a is provided with two surfaces 12e spaced apart from each other in the y direction and each facing in the z1 direction. As seen from FIG. 5, the surfaces 12e are at the same position as the latch projection 23a of the lancet holder 22 along the x1-x2 direction. As shown in FIG. 7, the lancet holder 22 is provided with a connecting portion 22b located at the same position as the sliding arm 23 along the x1-x2 direction. The connecting portion 22b is offset from the sliding arm 23 in the z2 direction. As discussed below, the lancet holder 22 receives a force directed in the z2 direction when the sliding arm 23 receives a force directed in the z2 direction from the protrusion 13 and elastically deforms. In this case, the z2 direction facing surfaces of the connecting portion 22b come into contact with the surfaces 12e of the rib 12d of the first part 12a. Accordingly, the lancet holder 22 is prevented from being unduly bent or unduly deviating from the desired center position. As noted below, the resistance against the reciprocating motion of the lancet holder 22 is mainly provided by the friction between the protrusion 13 and the inclined surface 23b of the sliding arm 23, though a certain frictional force may occur between the surfaces 12e of the rib 12d of the first part 12a and the connecting portion 22b of the lancet holder 22.

Figure 10:
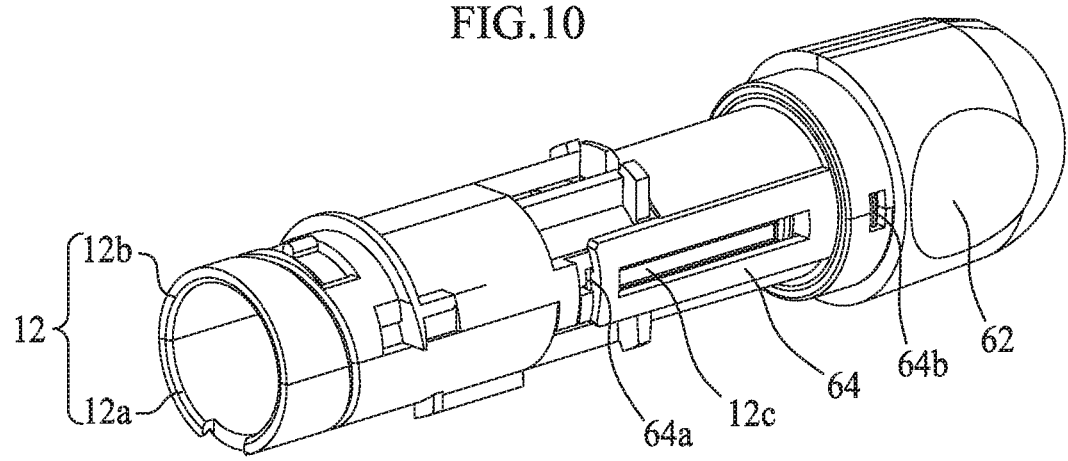
FIG. 10 is a perspective view depicting the inner frame, the sliding member and the setting member of the lancing device.
Figure 10:
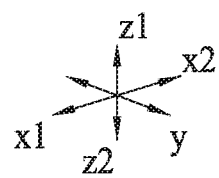
Figure 11:
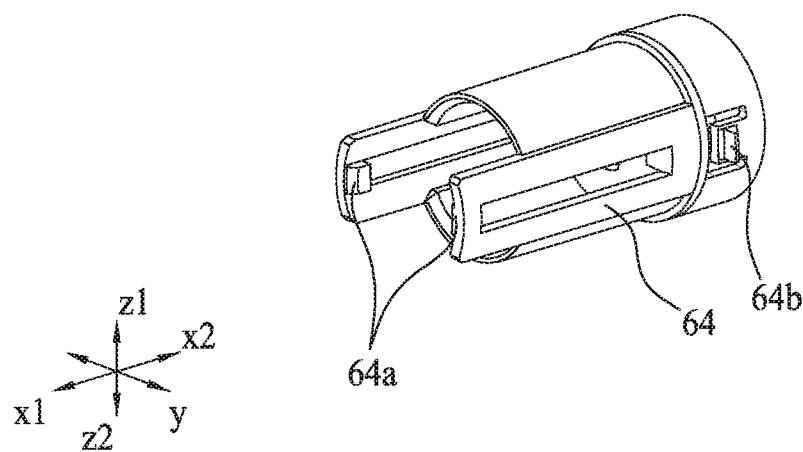
FIG. 11 is a perspective view depicting the sliding member of the lancing device.
Figure 11:
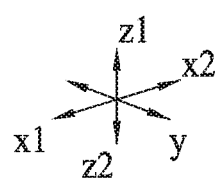

FIG. 10 is a perspective view depicting the inner frame 12, the setting member 62 and the slide member 64. FIG. 11 is a perspective view depicting the slide member 64. In the one end (in FIG. 11, the right-side end) of the slide member 64, two engaging parts 64b are formed, which are spaced apart from each other in the lateral direction (in FIG. 11, the y direction) perpendicular to the lancing direction (only one engaging part 64b is seen in FIG. 11). Each of these engaging parts 64b comes into engagement with an aperture formed in the setting member 62, as shown in FIG. 10, whereby the setting member 62 and the slide member 64 are fixed to each other. As described below, the setting member 62 and the slide member 64 as a whole are caused to slide relative to the inner frame 12.

Figure 12:
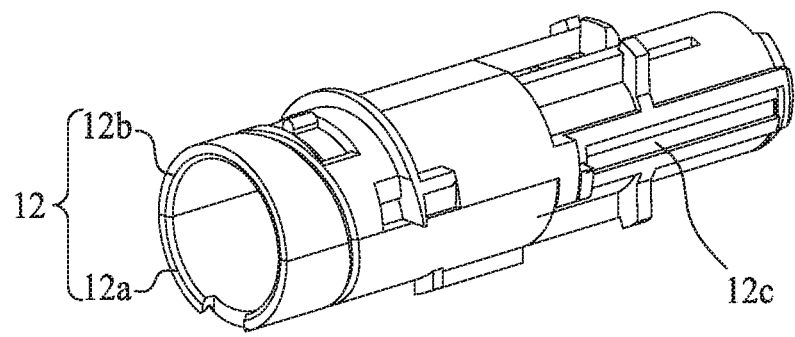
FIG. 12 is a perspective view depicting the inner frame of the lancing device.
Figure 12:
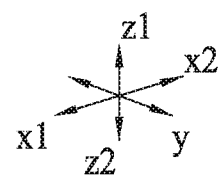
Figure 13:
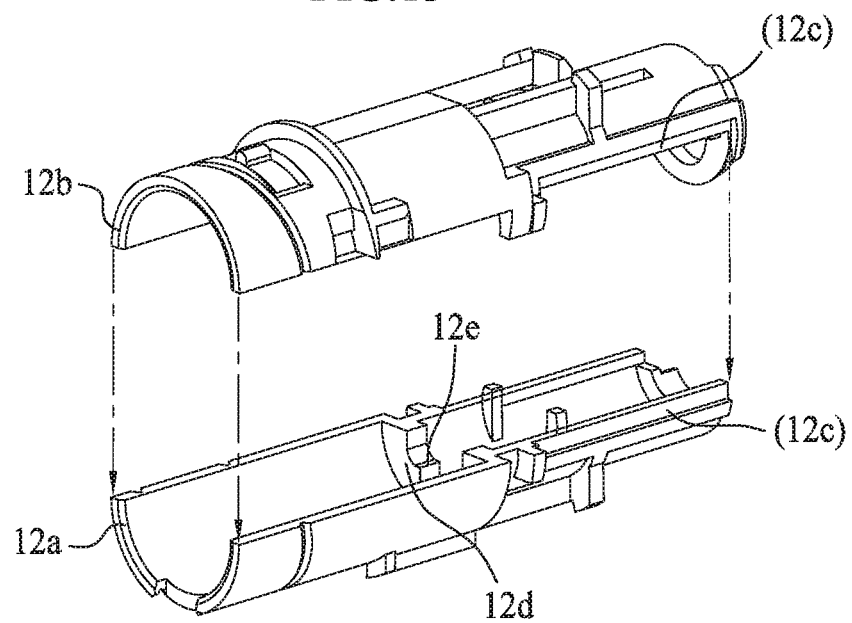
FIG. 13 is an exploded perspective view depicting the inner frame of the lancing device.
Figure 13:
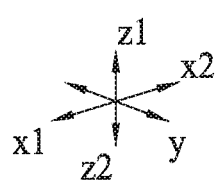

FIG. 12 is a perspective view depicting the inner frame 12, and FIG. 13 is an exploded perspective view of the inner frame 12. On the outer surface of the inner frame 12, two guide grooves 12c are formed, which are spaced apart from each other in the lateral direction (the y direction). Each guide groove 12c extends in the lancing direction (the x1-x2 direction). As shown in FIG. 13, each of the first part 12a and the second part 12b is formed with an elongated recess for constituting the guide groove 12c. When the first part 12a and the second part 12b are assembled, one recess of the first part 12a and the cooperating recess of the second part 12b are combined to provide a guide groove 12c.

As shown in FIG. 11, two guide projections 64a, spaced apart from each other in the lateral direction (y direction), are formed at an end of the slide member 64. As shown in FIG. 10, each of the guide projections 64a is jutted into a corresponding one of the guide grooves 12c of the inner frame 12. Thus, the slide member 64 (and hence the setting member 62) can slide relative to the inner frame 12 in the x1-x2 direction. The stroke of the slide member 64 depends on the length of the guide groove 12c and the size of the guide projection 64a. By moving the setting member 62 backward (i.e., in the x2 direction) relative to the inner frame 12, the lancing unit 2 can be brought into the standby state.

The sliding mechanism of the slide member 64 relative to the inner frame 12 is not limited to the embodiment described above. For example, the inner frame 12 may be formed as a single integral unit, and slits, instead of the guide grooves 12c, are formed in the inner frame 12 in a manner such that each slit extends through the thickness of the wall of the inner frame 12. The guide projections 64a of the slide member 64 may be brought into engagement with these slits, respectively. In another embodiment, instead of the inwardly projecting guide projections 64a, the slide member 64 may be formed with outwardly projecting guide projections, and these guide projections may be fitted into the respective slits from the inside of the inner frame 12 so as to extend toward the outside of the inner frame 12.

Next, the reciprocating motion of the lancing unit 2 in the lancing device A1 will be described below.

First, as shown in FIG. 3, the lancing unit 2 is set into the standby state. In this state, the progress spring 31 is compressed between the inner frame 12 and the lancet holder 22, and the latch projection 23a of the sliding arm 23 abuts against the protrusion 13 of the inner frame 12 (see FIG. 4). Thus, the lancing unit 2 is prevented from advancing in the lancing direction (the x1 direction).

Figure 14:
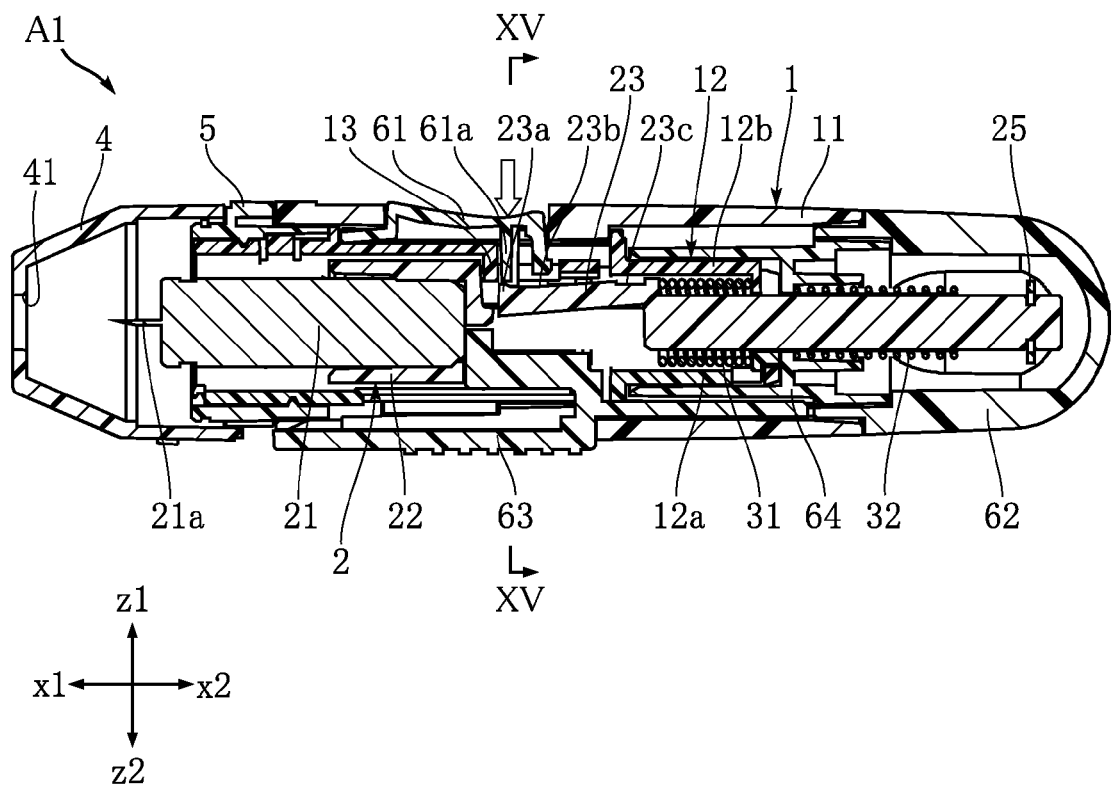
FIG. 14 is a sectional view depicting the standby state of the lancing device.
Figure 15:
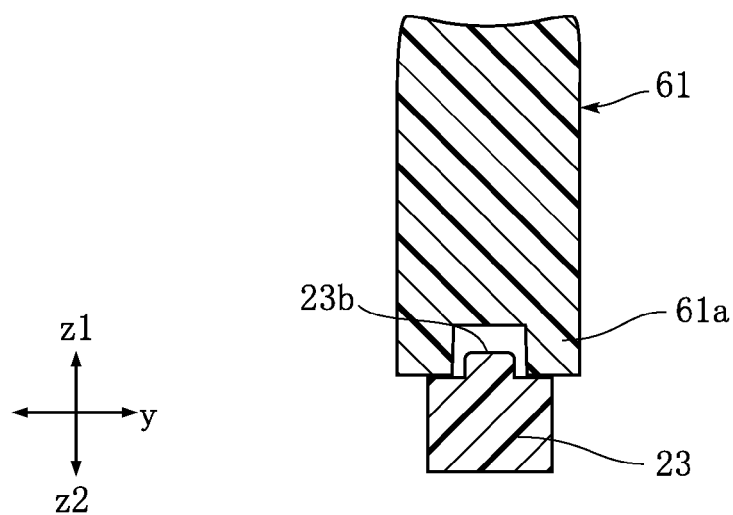
FIG. 15 is a sectional view taken along line XV-XV in FIG. 14, showing some features only.

Then, the distal end of the cover 4 is brought into contact with the skin. In this state, as shown in FIG. 14, the user pushes the puncture button 61. The puncture button 61 is provided with a presser piece 61a projecting inward (in the z2 direction). The pressure piece 61a pushes the free end of the sliding arm 23 in the z2 direction. Thus, the sliding arm 23 is bent in the z2 direction, whereby the sliding arm 23 is released from the engagement with the protrusion 13. FIG. 15 is a sectional view taken along the XV-XV line of FIG. 14 and shows only the sliding arm 23 and the puncture button 61. As shown in the figure, the inclined surface 23b is located only at a center of the sliding arm 23 in the y direction, and two elongated surfaces lower than the inclined surface 23b are formed to flank the inclined surface 23b in the y direction. Thus, as seen from FIG. 15, the sliding arm 23 has a ridge or raised portion providing the inclined surface 23b. On the other hand, a central recess (extending through in the x1-x2 direction) is formed in the tip surface (in FIG. 15, the lower surface) of the presser piece 61a near the central part. When the presser piece 61a comes into contact with the sliding arm 23, the recess of the presser piece 61a accommodates the above-mentioned ridge (providing the inclined surface 23b) of the sliding arm 23 in a manner such that the wall surface defining the recess is spaced apart from the ridge. Accordingly, the presser piece 61a pushes down the sliding arm 23 without touching the inclined surface 23b.

Figure 16:
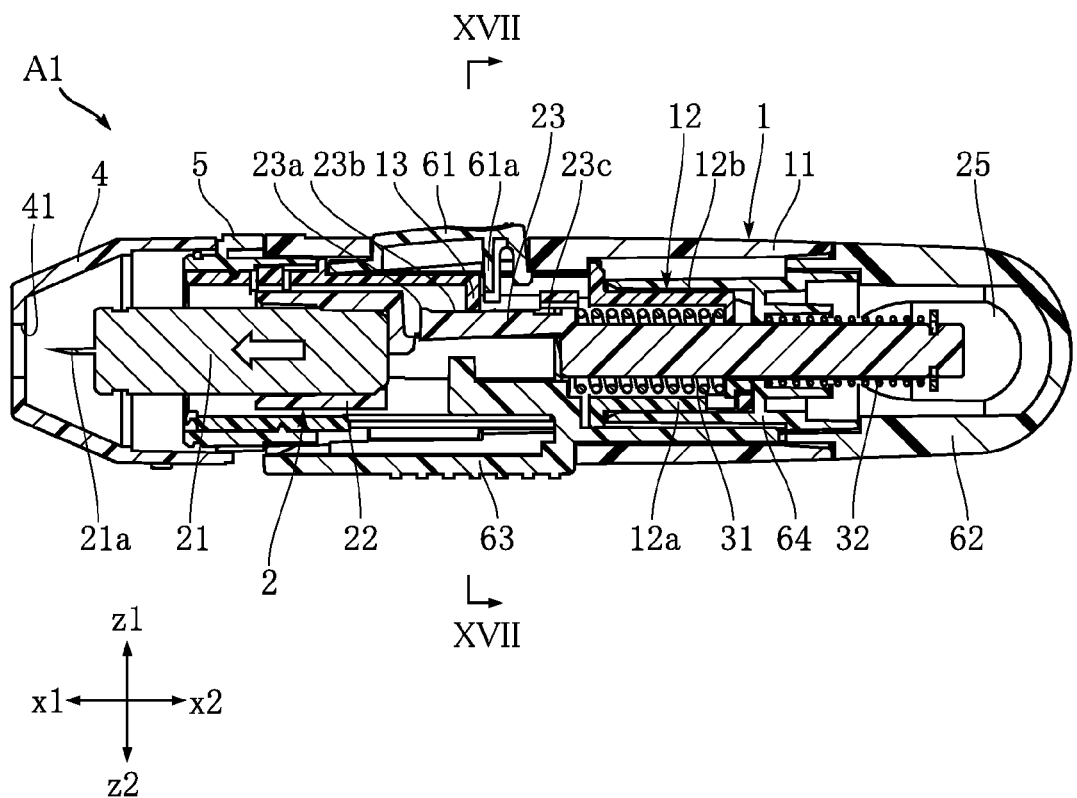
FIG. 16 is a sectional view depicting an advancing state of the lancing device.
Figure 17:
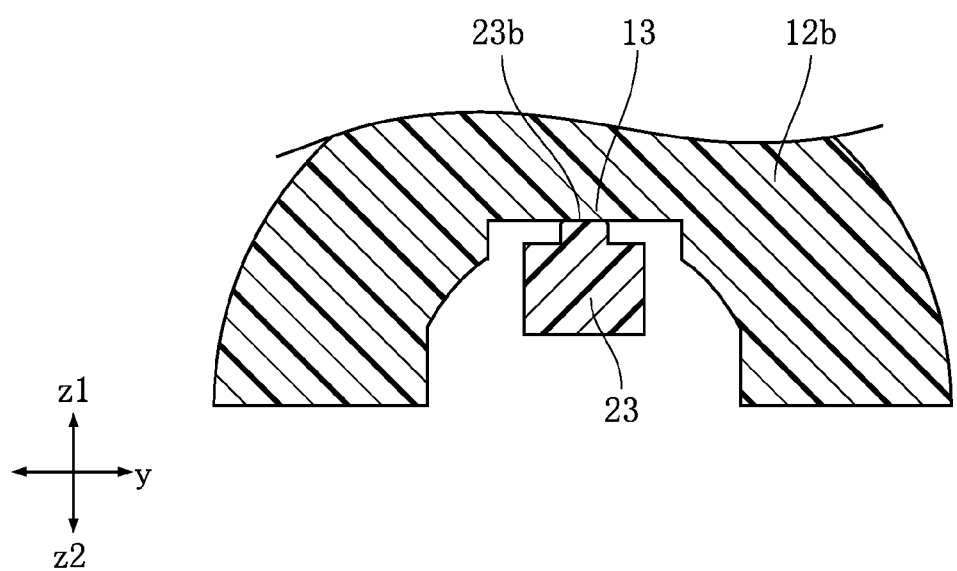
FIG. 17 is a sectional view taken along line XVII-XVII in FIG. 16, showing some features only.

When the sliding arm 23 is out of engagement with the protrusion 13 by the puncture button 61, the lancing unit 2 is caused to advance by the progress spring 31 in the lancing direction (the x1 direction), as shown in FIG. 16. At this stage, the inclined surface 23b of the sliding arm 23 is in sliding contact with the protrusion 13 of the second part 12b. FIG. 17 is a sectional view taken along the XVII-XVII line of FIG. 16, and shows only a part of the second part 12b and the sliding arm 23. The end surface (in FIG. 17, the lower surface) of the protrusion 13 is perpendicular to the z1-z2 direction, and has a width (the size measured in the y direction) greater than the width of the inclined surface 23b. Thus, in the y direction, the entirety of the inclined surface 23b is brought into contact with the protrusion 13. As seen from FIGS. 16 and 17, the protrusion 13 is provided by apart of the rib formed on the second part 12b. Thus, the protrusion 13 has relatively high rigidity. On the other hand, the sliding arm 23 is cantilevered, and therefore elastically deformable. Thus, while the sliding arm 23 and the protrusion 13 are being in sliding contact with each other, the sliding arm 23 is slightly bent in the z2 direction.

As described above, a combination of the protrusion 13 and the inclined surface constitutes a resistance generator, and the friction between the protrusion 13 and the inclined surface 23b will be applied as a resistance against the motion of the lancing unit 2. The resistance against the lancing unit 2 can result from friction between other members held in sliding contact, but such friction is substantially negligible in comparison with the friction between the protrusion 13 and the inclined surface 23b.

Figure 18:
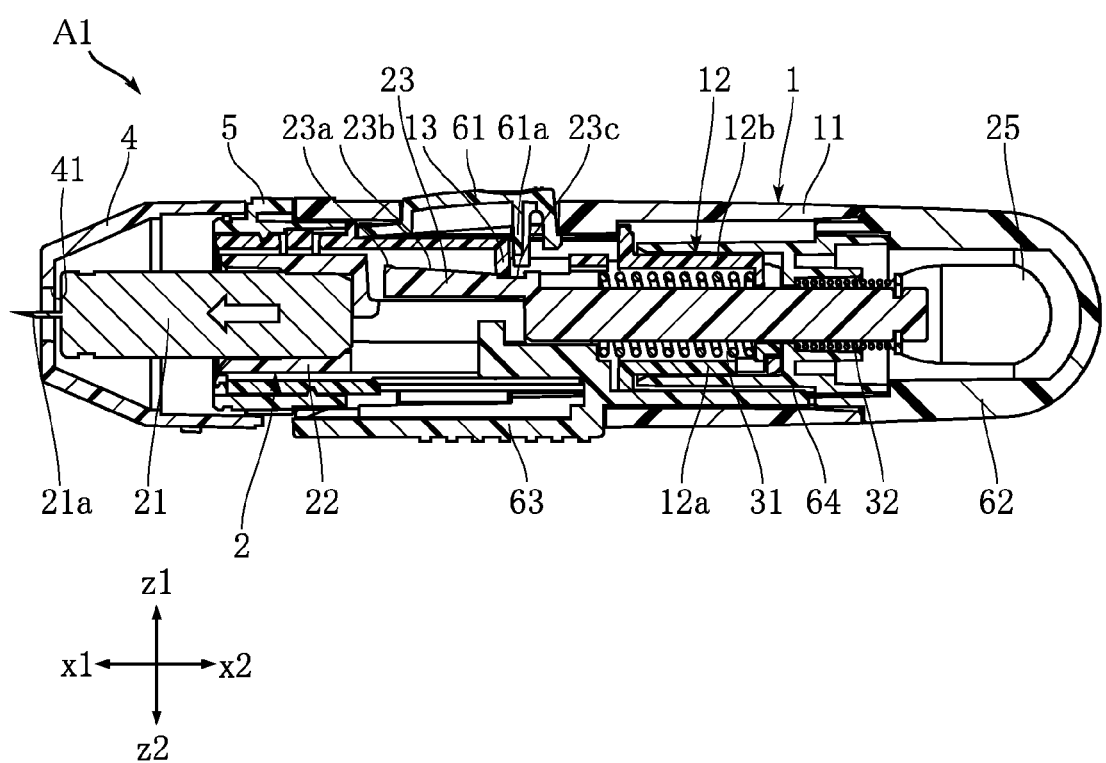
FIG. 18 is a sectional view depicting a lancing state of the lancing device.

FIG. 18 shows a state in which the lancing unit 2 advances further in the x1 direction. At this stage, the protrusion 13 has passed the inclined surface 23b and is located at the same position as the recess 23c along the x1-x2 direction (see FIG. 20D). As noted above, the bottom surface of the recess 23c is located offset in the z2 direction from the tip of the protrusion 13, and therefore the protrusion 13 does not contact with the recess 23c (precisely, the wall surface defining the recess 23c). That is, in the state shown in FIG. 18, the protrusion 13 and the sliding arm 23 are out of contact with each other, thereby generating no friction between the protrusion 13 and the sliding arm 23. In other words, the resistance generator generates zero resistance in the state shown in FIG. 18.

FIG. 18 shows the limit position (referred to as the "puncture point") the lancing unit 2 can arrive at in the lancing direction. At this stage, the tip of the needle 21a protrudes beyond the distal end of the cover 4, whereby the needle 21a can prick the skin.

Figure 19:
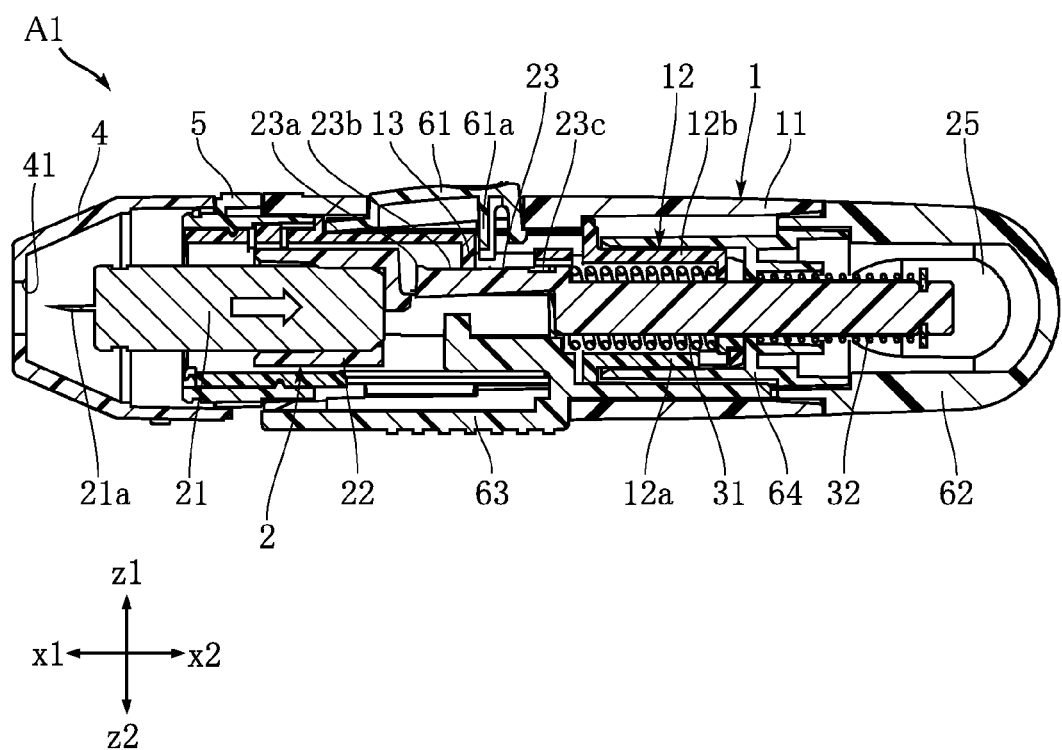
FIG. 19 is a sectional view depicting a retreating state of the lancing device.

As the lancing unit 2 advances in the x1 direction, the retreat spring 32 is being compressed while the progress spring 31 is being released from the compression state. The retreat spring 32 is compressed between the washer 25 attached to the lancet holder 22 and the slide member 64. Thus, after arriving at the puncture point, the lancing unit 2 is caused to retreat (i.e., move in the x2 direction) by the retreat spring 32, as shown in FIG. 19.

As explained above, in use, the lancing unit 2 reciprocates in the housing 1 (the inner frame 12), that is, advances in the x1 direction and retreats in the x2 direction with the puncture point as a turnaround point.

Next, the resistance against the reciprocating motion of the lancing unit 2 is described below with reference to FIGS. 20A-G.

Figure 20A:
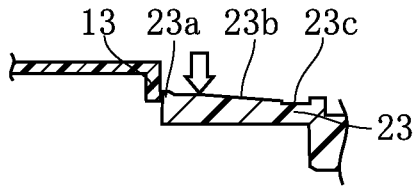
FIGS. 20A-20F illustrate, in section, the positional relation between the sliding member (sliding arm) and the protrusion to be held in sliding contact with the sliding member.
Figure 20B:
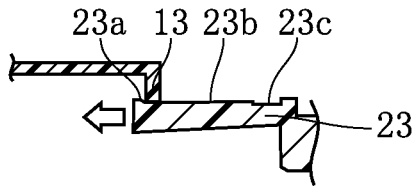
Figure 20C:
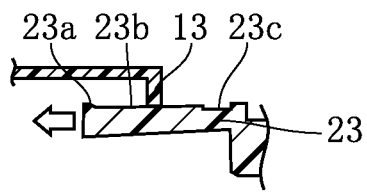
Figure 20D:
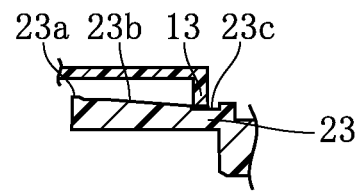
Figure 20E:
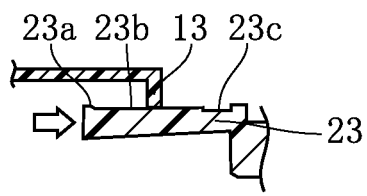
Figure 20F:
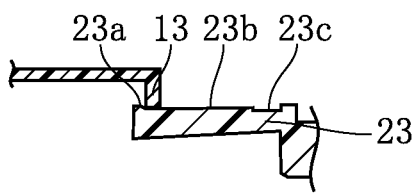

FIGS. 20A-F show the relation between the protrusion 13 and the sliding arm 23 while the lancing unit 2 is being reciprocating in the housing 1. Fig. G shows how the resistance against the reciprocating motion of the lancing unit 2 changes. The standby state for initiating the lancing is shown in FIG. 20A, which corresponds to the state shown in FIG. 3. FIG. 20B shows the state in which the sliding arm 23 is released from the engagement with the protrusion 13 upon the pushing of the puncture button 61 (see FIG. 14). FIG. 20C shows a state in which the lancing unit 2 is advancing in the x1 direction, with the protrusion 13 and the inclined surface 23b being held in sliding contact with each other. The state shown in FIG. 20C corresponds to that shown in FIG. 16. FIG. 20D shows a state in which the lancing unit 2 is at the puncture point (see FIG. 18). FIG. 20E shows a state in which the lancing unit 2 is being retreating (moving in the x2 direction) with the protrusion 13 and the inclined surface 23b being in sliding contact with each other. It should be noted that the position of the lancing unit 2 relative to the housing 1 along the x1-x2 direction is the same with FIG. 20C and FIG. 20E. FIG. 20F shows a state in which the retreat of the lancing unit 2 has been completed. The position of the lancing unit 2 relative to the housing 1 along the x1-x2 direction is the same with FIG. 20B and FIG. 20F.

Figure 20G:
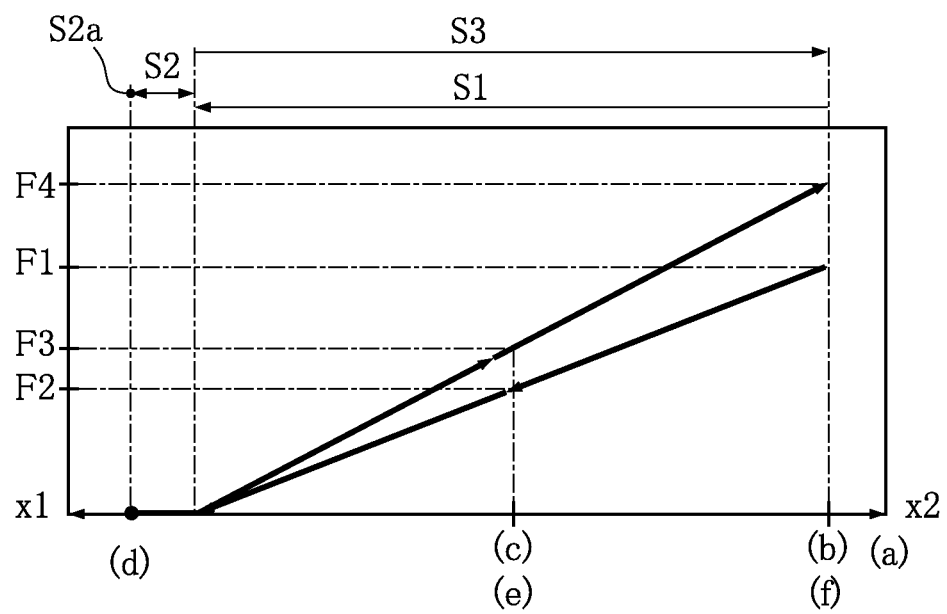
FIG. 20G is a graph illustrating the resistance resulting from the sliding contact between the sliding member and the protrusion.

In FIG. 20G, the horizontal axis indicates the position of the lancing unit 2 along the x1-x2 direction, and the vertical axis indicates the resistance provided by the resistance generator. The advance section S1 shown in the figure corresponds to a path over which the lancing unit 2 moves in the x1 direction after leaving from the standby state (FIG. 20A). The initial point of the advance section S1 corresponds to the time when the protrusion 13 begins to come into sliding contact with the inclined surface 23b, the end point of the advance section S1 corresponds to the time when the sliding contact of the protrusion 13 with the inclined surface 23b is over (FIG. 20B).

The puncture section S2 follows the advance section S1 noted above. The initial point of the puncture section S2 coincides with the endpoint of the advance section S1. Thus, the puncture section S2 begins when the protrusion 13 gets completely spaced apart from the inclined surface 23b. In the puncture section S2, the protrusion 13 has shifted over the recess 223c along the x1-x2 direction, and therefore shares the same position with the recess 23c along the x1-x2 direction. The puncture section S2 includes the puncture point S2a or the end point of the advancement of the lancing unit 2. Upon arriving at the puncture point S2a, the lancing unit 2 begins to retreat. The end point of the puncture section S2 corresponds to the when the protrusion 13 gets back into sliding contact with the inclined surface 23b.

The retreat section S3 follows the puncture section S2. The initial point of the retreat section S3 corresponds to the time when the protrusion 13 gets back into sliding contact with the inclined surface 23b. In the retreat section S3, the lancing unit 2 moves in the x2 direction, and the protrusion 13 is in sliding contact with the inclined surface 23b. The end point of the retreat section S3 corresponds, in the illustrated embodiment, to the time when the positional relation between the protrusion 13 and the sliding arm 23 is the same as that occurring at the initial point of the advance section S1.

For the advance section S1, the sliding contact between the protrusion 13 and the inclined surface 23b provides a frictional force or resistance F against the motion of the lancing unit 2. In the state shown in FIG. 20B, the bend of the sliding arm 23 becomes maximum, and the resistance F takes a value F1. As the lancing unit 2 advances, the resistance F gradually becomes small. This is because the bend of the sliding arm 23 gradually becomes small due to the slant of the inclined surface 23b. For example, in the state shown in FIG. 20C, the resistance F takes a value F2 which is smaller than the value F1. The resistance F decreases gradually from the initial value F1 until it becomes 0 at the end point of the advance section S1. In the illustrated embodiment, the resistance F decreases linearly from F1 to 0.

The lancing unit 2 advances further into the puncture section S2, where the recess 23c and the protrusion 13 are out of contact with each other, thereby rendering the resistance F remain 0. Thus, in the puncture section S2 where the lancing unit 2 slightly moves forward and backward with the puncture point S2a as the turnaround point, the resistance generator does not apply any resistance to the lancing unit 2.

Then, the lancing unit 2 retreats into the retreat section S3, where the protrusion 13 comes back into sliding contact with the inclined surface 23b. Thus, the resistance F gradually increases from zero at the initial point of the retreat section S3. For example, in the state shown in FIG. 20E, the resistance F takes a value F3 (>F2). At the endpoint of the retreat section S3 (see the state shown in FIG. 20F), the resistance F takes a value F4 (>F1).

As seen from FIG. 20G, the resistance F (=0) for the puncture section S2 is smaller than the resistance F taken at any point in the retreat section S3, and also than the resistance F taken at any point in the advance section S1. Further, the mean value (=0) of the resistance F in the puncture section S2 is smaller than the mean value of the resistance F in the retreat section S3, and also than the mean value of the resistance F in the advance section S1.

Figure 21:
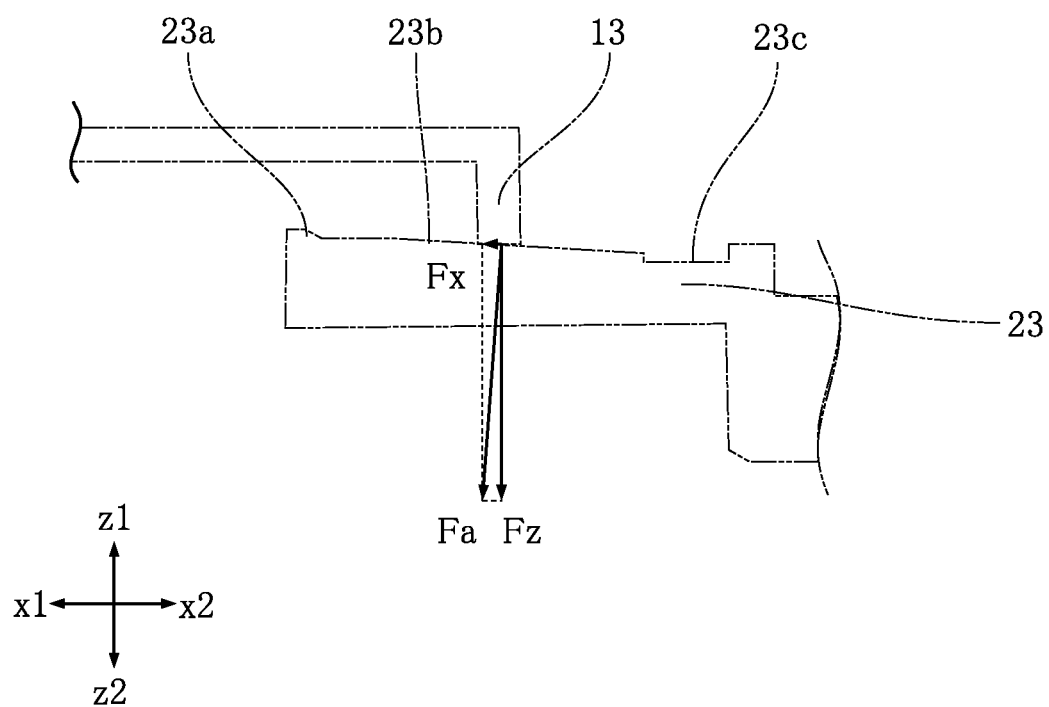
FIG. 21 is a sectional view illustrating the mechanism of the resistance occurrence by the resistance generator of the lancing device.
Figure 22:
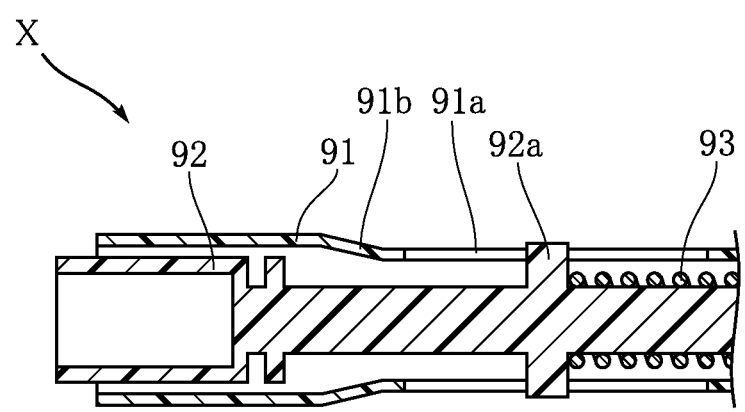
FIG. 22 is a sectional view illustrating a known lancing device.

The relation between the resistance F in the advance section S1 and the resistance F in the retreat section S3 will now be described with reference to FIG. 21. FIG. 21 depicts the protrusion 13 and the sliding arm 23 (two-dot chain lines) in the advance section S1 or the retreat section S3. The protrusion 13 and the sliding arm 23 contact with each other, and thus a normal force acts between them. The normal force Fa depicted in the figure acts on the sliding arm 23 from the protrusion 13. The direction of the normal force Fa is parallel to the normal direction of the inclined surface 23b in which the inclined surface 23b faces. The normal force Fa can be resolved into two components: a component Fz along the z1-z2 direction and a component Fx along the x1-x2 direction. The component Fx, which is non-zero, describes the influence directed in the x1 direction. Thus, the lancing unit 2 will be urged in the x1 direction corresponding to the component Fx when the protrusion 13 and the inclined surface 23b are in sliding contact in the advance section S1 and the retreat section S3. In addition to this urging force, a kinetic friction force (="dynamic friction coefficient" times the normal force Fa) is also applied. Thus, when the protrusion 13 and the inclined surface 23b are in sliding contact, a sum of the urging force due to the component Fx and the kinetic friction force will be applied to the lancing unit 2. As is known, frictional force acts against the motion of the lancing unit 2. Thus, when the lancing unit 2 advances in the advance section S1, the kinetic friction force is directed (substantially) in the x2 direction, and the urging force due to the component Fx is directed in the x1 direction. Accordingly, a net force of the kinetic friction force minus the urging force is applied to the lancing unit 2. Thus, for the advance section S1, the resistance F against the motion of the lancing unit 2 becomes slightly smaller than the kinetic friction force in itself. On the other hand, when the lancing unit 2 retreats in the retreat section S3, a net force of the kinetic friction force plus the urging force is applied to the lancing unit 2. Thus, the resistance F against the motion of the lancing unit 2 becomes slightly greater than the kinetic friction force in itself. As a result, as shown in FIG. 20G, the resistance F4 is greater than the resistance F1, and the resistance F3 is greater than the resistance F2. The same principle applies at any other position for the advance section S1 and the retreat section S3. That is, the resistance F in the retreat section S3 is greater than the resistance F in the advance section S1 when the positional relation between the protrusion 13 and the inclined surface 23b is the same for the two sections.

Also, another reason can be given for the fact that the resistance F is different for the advance section S1 and the retreat section S3 can be as follows. In the advance section S1, the bending of the sliding arm 23 is maximum at the initial point, and then becomes less as the lancing unit 2 advances. On the other hand, in the retreat section S3, the bending of the sliding arm 23 is minimum (=0) at the initial point, and then becomes more as the lancing unit 2 retreats. In other words, in the advance section S1 the sliding arm 23 releases the stored energy, while in the retreat section S3 the sliding arm 23 stores energy. Accordingly, the resistance F becomes greater for the retreat section S3 than for the advance section S1.

Advantages of the lancing device A1 will now be described below.

According to the present embodiment, the resistance F applied to the lancing unit 2 in the puncture section S2 is relatively small (preferably, zero). Thus, the pricking speed of the needle 21a is not unduly reduced. Also, after the skin is pricked by the needle 21a, the lancing unit 2 will properly retreat, which is advantageous to drawing the needle 21a away from the skin. In the retreat section S3, on the other hand, the resistance F applied to the lancing unit 2 is relatively large. Accordingly, in the retreat section S3, the retreating momentum of the lancing unit 2 can be properly damped. Thus, the speed of the lancing unit 2 can be reduced sufficiently (or even to zero) as the lancing unit 2 approaches the endpoint of the retreat section S3. Thus, it is possible to prevent the lancing unit 2 from unduly vibrating at or near the end point of the retreat section S3 after the pricking of the skin is performed.

As noted above, with the lancing device A1, it is possible to prevent the needle 21a from remaining stuck in the skin. Also, after the skin is pricked, unnecessary vibrations of the lancing unit 2 will not occur or be properly checked, which is advantageous to preventing the user from feeling unpleasant in using the device.

In the illustrated embodiment, a certain resistance F is allowed to be applied to the lancing unit 2 even in the advance section S1. That is, the protrusion 13 and the inclined surface 23b are in sliding contact with each other in the advance section S1, too. Such an arrangement is advantageous to preventing the mechanism of the resistance generator from becoming unduly complicated, and hence advantageous to the downsizing of the lancing device A1.

In the puncture section S2, the resistance F applied to the lancing unit 2 (and hence the lancet 21) is zero. Thus, it is possible to cause the needle 21a to prick the skin with proper momentum, and then to be pulled away from the skin swiftly.

The sliding configuration by the protrusion 13 and the cantilevered sliding arm 23 is advantageous to making the lancing device A1 simple and compact. Also, it is possible to generate a desired value of resistance F applied in the advance section S1 and the retreat section S3 by providing the sliding arm 23b with an inclined surface 23b. The recess 23c is advantageous to ensuring that the resistance F in the puncture section S2 is zero. The sliding arm 23 serves not only as (a part of) the resistance generator, but as an engaging element (for engaging the lancing unit 2 with the housing 1) by being provided with a latch projection 23a. Such a configuration is also advantageous to the downsizing of the lancing device A1.

The configurations of the lancing device are not limited to those of the embodiment explained above. Various variations and modifications may be made without departing from the scope of the present invention.

The invention claimed is:

1. A lancing device comprising:
a housing;
a lancing unit capable of reciprocating relative to the housing, the reciprocating including an advancing motion and a retreating motion, the lancing unit being provided with a lancing element to prick skin of a subject;
an elastic member for causing the lancing unit to reciprocate; and
a resistance generator for applying resistance to the lancing unit;
wherein a reciprocating motion of the lancing unit includes a puncture section and a retreat section following the puncture section, the puncture section including a puncture point at which the lancing element pricks the skin, and
wherein the resistance generator is configured to apply a greater resistance in the retreat section than in the puncture section,
wherein the resistance generator includes a protrusion and a sliding member held in sliding contact with the protrusion in the retreat section,
wherein one of the protrusion and the sliding member is provided on the housing, and the other of the protrusion and the sliding member is provided on the lancing unit,
wherein the sliding member has an inclined surface, and the protrusion is held in sliding contact with the inclined surface so that the resistance applied to the lancing unit becomes greater in the retreat section than in the puncture section.

2. The lancing device according to claim 1, wherein the reciprocating motion of the lancing unit includes an advance section followed by the puncture section, and the resistance generator is configured to apply a greater resistance in the advance section than in the puncture section.

3. The lancing device according to claim 2, wherein the resistance generator is configured to apply a greater resistance in the retreat section than in the advance section when a positional relation between the lancing unit and the housing is same for the retreat section and the advance section.

4. The lancing device according to claim 1, wherein the resistance generator is configured to apply zero resistance in the puncture section.

5. The lancing device according to claim 1, wherein the sliding member is more elastically deformable in a direction in which the sliding member faces the protrusion than is the protrusion.

6. The lancing device according to claim 5, wherein the sliding member includes a fixed end and a free end spaced apart from each other in a reciprocating direction of the lancing unit, the fixed end being adjacent to the protrusion when the lancing unit is at the puncture point, the free end being adjacent to the protrusion when the lancing unit is at an end point of the retreat section, and
wherein the sliding member is provided with an inclined surface arranged between the fixed end and the free end and coming into sliding contact with the protrusion, the inclined surface being inclined so as to be closer to the protrusion in a direction perpendicular to the reciprocating direction as proceeding from the fixed end toward the free end.

7. The lancing device according to claim 1, wherein the sliding member is configured as an engaging element for engaging the housing and the lancing unit with each other so that the lancing unit is held at the end point of the retreat section.

8. The lancing device according to claim 1, wherein the protrusion is provided on the housing, and the sliding member is provided on the lancing unit.

9. The lancing device according to claim 8, wherein the housing includes an outer frame and an inner frame disposed in the outer frame, and the protrusion is provided on the inner frame.

10. The lancing device according to claim 1, wherein
the protrusion is provided on and extending from a sidewall of one of the housing and the lancing unit toward the other one of the housing and the lancing unit in a direction perpendicular to a central axis of the one of the housing and the lancing unit, and
a sliding member has an arm portion having a free end and a fixed end fixed to the other one of the housing and the lancing unit, the arm portion having the inclined surface.

11. The lancing device according to claim 1, wherein
the protrusion is provided on one of the housing and the lancing unit, the sliding member has an arm portion having a free end and a fixed end fixed to the other one of the housing and the lancing unit, the arm portion having the inclined surface, and the arm portion has a recess between the inclined surface and the fixed end.

12. The lancing device according to claim 1, wherein the protrusion is provided on one of the housing and the lancing unit, the sliding member has an arm portion having a free end and a fixed end fixed to the other one of the housing and the lancing unit, the arm portion having the inclined surface, the arm portion has a projection disposed at the free end, and the inclined surface is positioned between the projection and the fixed end.

* * * * *